United States Patent [19]
Ning

[11] Patent Number: 5,212,585
[45] Date of Patent: May 18, 1993

[54] LASER PROTECTIVE DEVICE
[75] Inventor: Xiaohui Ning, N. Providence, R.I.
[73] Assignee: American Optical Corporation, Southbridge, Mass.
[21] Appl. No.: 503,873
[22] Filed: Apr. 3, 1990
[51] Int. Cl.$^5$ .............................. G02F 1/03
[52] U.S. Cl. .................... 359/276; 359/250; 359/246
[58] Field of Search .......... 359/245, 246, 250, 276, 359/359, 582, 588

[56] References Cited
U.S. PATENT DOCUMENTS

| | | | |
|---|---|---|---|
| 3,726,585 | 4/1973 | Fedotowsky et al. | 350/356 |
| 3,989,355 | 11/1976 | Wilmer | 350/335 |
| 4,240,696 | 12/1980 | Tracy et al. | 359/578 |
| 4,247,166 | 1/1981 | Yeh | 359/263 |
| 4,589,737 | 5/1986 | Sashital | 350/356 |
| 4,786,128 | 11/1988 | Birnbach | 359/245 |
| 4,985,179 | 1/1991 | Seo et al. | 350/353 |
| 5,002,369 | 3/1991 | Sakata | 350/355 |
| 5,054,892 | 10/1991 | Takanashi et al. | 359/245 |

FOREIGN PATENT DOCUMENTS
0358229 3/1990 European Pat. Off. .......... 359/245

Primary Examiner—Rolf Hille
Assistant Examiner—Tan Ho
Attorney, Agent, or Firm—Fishman, Dionne & Cantor

[57] ABSTRACT

A laser sensor protector is provided comprising a non-linear dynamic device which has a flat broad band reflectance covering the entire visible range in the on-state and allows for good optical quality and high transmittance (80-90) in the off-state. The device can be constructed using electro-optic materials or nonlinear optical materials. If electro-optical materials, i.e., those for which the refractive index can be controlled by an external field, or nonlinear optical materials, i.e, those for which the refractive index can be controlled by the light intensity, are used to construct the present invention, it is possible to achieve dynamic switching, that is, the device is clear in the off-state and it is highly reflective over a broad band in the on-state.

16 Claims, 8 Drawing Sheets

LASER PROTECTIVE DEVICE

BACKGROUND OF THE INVENTION

This invention relates generally to the field of sensor protection including protective eyewear. More particularly, this invention relates to a new and improved protective filter which prevents lasers from damaging the eyes and other sensors.

The increased use of tunable and chirped lasers as range finders, target designators and directed energy weapons (DEW) in the battlefield creates a serious threat to equipment sensors and soldier's eyes. To provide effective protection to such sensors (eyes), a device must have a broad rejection band (or a tunable, narrow band) in addition to fast response, good optical quality and high transmittance in the off-state.

Harmful laser radiation can be prevented from reaching sensors including the human eyes by a number of approaches. If the wavelengths of lasers are known in advance, it is usually possible to use absorptive dyes or fixed wavelength narrow notch reflectors to protect the sensors. Both absorptive glasses and Plastics with synthetic dyes may be used to selectively absorb harmful laser radiation. This approach is particularly attractive if the wavelengths of the lasers are outside the spectral range at which the sensor is designed to operate. However, if the wavelengths of the lasers are inside the spectral range of the sensor, the preferred approach is to use narrow notch reflectors at the required wavelength(s) in the form of dielectric thin films, or rugate filters or volume holographic notch reflectors because these filters provide greater transmittance over the spectral sensitive region of the sensor than absorptive dyes.

However, if the wavelengths of the lasers are not known in advance or the wavelengths of the lasers can be varied with time such as in the case of tunable lasers and chirped lasers, the above approaches will not provide effective protection to the sensor. New approaches that can block frequency agile lasers are required for effective sensor protection. Within the spectral sensitivity range of the sensor, the ideal device will only block harmful laser light at any wavelength from any angle with a high efficiency, and transmit background light completely. The device must have good optical quality and minimum coloration. For practical purposes, the device must also be compact and light weight. Furthermore, if the device actively switches between the blocking and the non-blocking states, the response should be sufficiently fast such that pulsed lasers can also be blocked.

A number of approaches has been suggested in the past. These include: nonlinear scattering, self-focusing, PLZT window, nonlinear absorption, coherence filter, sacrificial filter and a tunable narrow notch reflector. The last approach may be constructed using the approach suggested in U.S. Pat. No. 4,786,128. None of them appears to be ideal for the required application.

SUMMARY OF THE INVENTION

In accordance with the present invention, a laser sensor protector is provided comprising a nonlinear dynamic device which has a flat broad band reflectance covering the entire visible range in the on-state and allows for good visual acuity and high transmittance (80-90%) in the off-state. This device can be constructed using electro-optic materials or nonlinear optical materials. The device comprises a multilayer stack capable of acting as a broad band reflector wherein:

(1) the optical thickness of the layers are randomly varied; and (2) the refractive index of the layers are substantially similar in the off-state and substantially different in the on-state.

If electro-optical materials, i.e., those for which the refractive index can be controlled by an external field, or nonlinear optical materials, i.e, those for which the refractive index can be controlled by the light intensity, are used to construct the present invention, it is possible to achieve dynamic switching, that is, the device is clear in the off-state and it is highly reflective over a broad band in the on-state. Sensor devices in accordance with this invention can be made of alternating electro-optic and/or nonlinear optical materials for modulating the index or piezoelectric materials for modulating the thickness or both. If electro-optic materials are used, the switching is obtained by applying an external electrical field by using transparent electrodes at the surfaces or multiple electrode layers that are imbedded in the device. If nonlinear optical materials are used, the switching is accomplished by the intensity of the incident light. In this case, a self-activated device is formed. In the off-state the device is essentially transparent if the index is the same for all layers. In the on-state, the thickness/index distribution becomes completely random because of the electro-optic/electro mechanic and nonlinear optical effects, and thus the device reflects light over a broad band of wavelength with very high efficiency.

The above-discussed and other features and advantages of the present invention will be appreciated and understood from the following detailed description and drawings.

BRIEF DESCRIPTION OF THE DRAWINGS

Referring now to the drawings, wherein like elements are numbered alike in the several FIGURES.

DESCRIPTION OF THE PREFERRED EMBODIMENT

The present invention generally comprises sensor protection formed from a multilayer stack wherein (1) the optical thickness of the layers are randomly varied and (2) the refractive index of the layers are substantially similar in the off-state and differ in the on-state, so as to convert the multilayer stack to a broad band reflector. The multilayer stack may be formed from either (1) electro-optical materials whose refractive index is controlled by an external field or (2) nonlinear optical materials whose refractive index is controlled by light intensity. Alternatively, the stack may be formed from a combination of electro-optical and nonlinear optical materials. In either case, the protective eyewear device of this invention permits dynamic switching such that the device is substantially clear in the off-state and is highly reflective over a broad band in the on-state.

The physical principle of this invention can be summarized as follows. The interference between the multiple scattered waves in the medium confines the waves within a region of the localization length. If the size of the system is greater than the localization length, the diffusion coefficient for wave propagation goes to zero. The localization length depends on the wavelength of the wave as well as the variation of both the refractive index and layer thickness. The basic concept is to electronically or optically control the localization length by changing the thickness/index distribution such that, in the on-state, the localization length is smaller than the size of the system and the reverse is true in the off-state. By properly designing the multilayer structure, the localization length for light over a broad wavelength band can be controlled by an external electrical field if electro-optic materials are used, or by the incident light if nonlinear optical materials are used, and active switching can be achieved. An alternate view is to consider the device of this invention as a multiplexed filter with a large number of reflection lines covering a broad spectral range. The index profile of such a multiplexed filter is the sum of the index profiles of each individual line. The resulting index profile can be approximately represented by a random thickness/index distribution.

Figure 1:
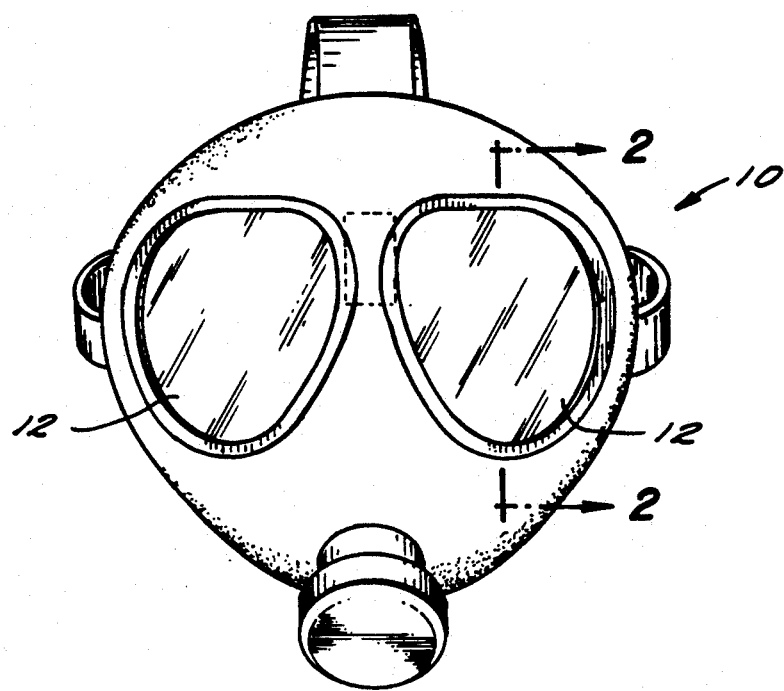
FIG. 1 is a perspective view of eyewear incorporating the laser protective device of the present invention.
Figure 2:
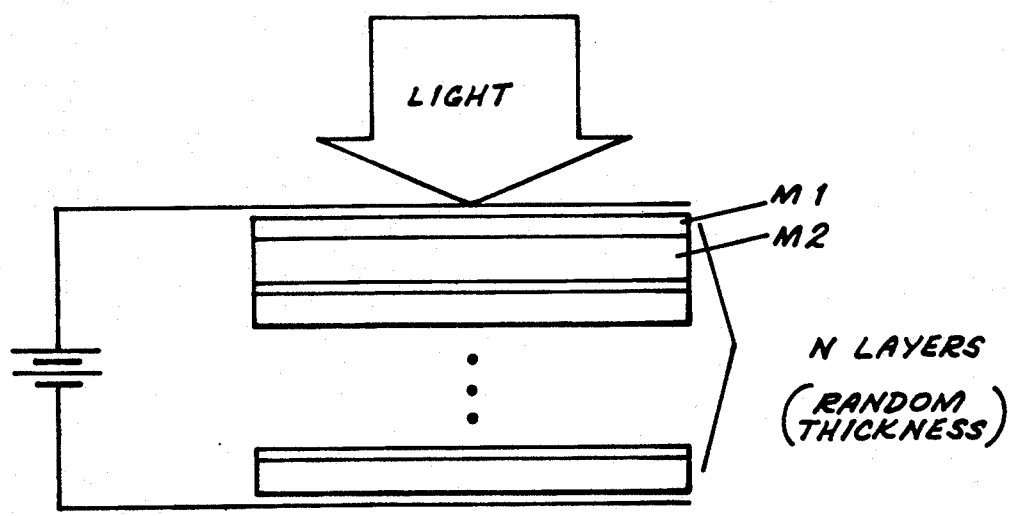
FIG. 2 is a diagrammatic cross-sectional elevation view along the line 2-2 of FIG. 1.
Figure 8:
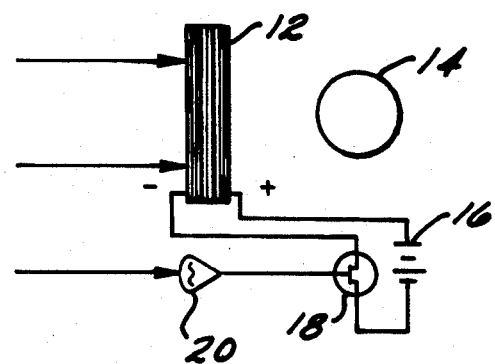
FIG. 8 is a schematic view of a laser protective device using electro-optical materials in accordance with the present invention.
Figure 9:
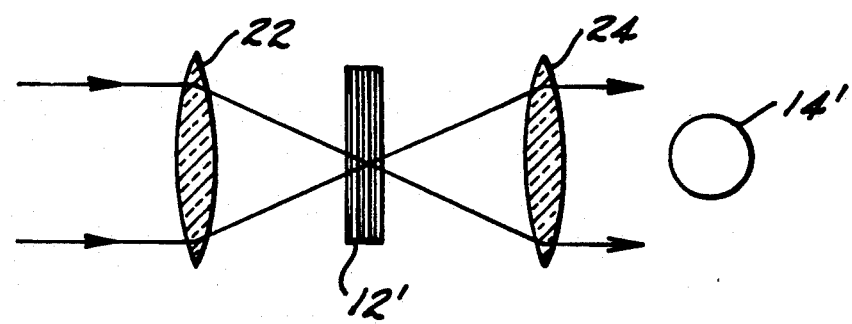
FIG. 9 is a schematic view of a laser protective device using nonlinear optical materials in accordance with the present invention.

A first embodiment of the protective eyewear device of this invention is shown in FIGS. 1 and 2. In FIGS. 8 and 9, generalized schematics of the present invention are shown. These schematics will be described in more detail hereinafter. In FIG. 1, eyewear depicted generally at 10 has a pair of lens 12 incorporating therein the protective multilayer stack of the present invention. FIG. 2 is a cross-sectional diagrammatic view through a lens 12 which comprises N alternating layers of two dynamic materials $M_1$ and $M_2$ (in the following, the term "dynamic" will refer to both electro-optic and nonlinear optical materials). Since the nonlinear optical effect is essentially equivalent to the electro-optic effect in the sense that they both cause a refractive index change, the following discussion assumes the electro-optic phenomenon. However, the results apply to the nonlinear optical materials as well. The refractive index of each material as a function of the external electrical field E can be described by the following equations:

$$N_1(E) = N_{10} + AE + \ldots \quad (1a)$$

$$N(E) = N_{20} + BE + \ldots \quad (1b)$$

where $N_{10}$ and $N_{20}$ are the off-state indices of $M_1$ and $M_2$ respectively. It is assumed that the electro-refractive coefficient A for material $M_1$ and B for material $M_2$ are equal in magnitude but opposite in sign. For simplicity, the intrinsic absorption for both $M_1$ and $M_2$ are assumed to be zero. The electric field is applied to the two transparent surface electrode layers. The optical thickness distribution can be either a uniform random distribution or Gaussian distribution. The optimal distribution is governed by the application requirements. For a uniform random distribution the average optical thickness and the range of fluctuation are two variables that must be determined. For a Gaussian distribution the average optical thickness and the standard deviation are the parameters that can be varied to optimize the performance. If, in the off-state, when no external electric field is applied, $M_1$ and $M_2$ are index matched and the protective device of this invention is completely transparent. Practically, there may not be a perfect index match and a small index difference $N_{10}-N_{20}$ will exist. The effect of a non-zero index difference will be discussed in more detail below. In the on-state, when an external field is applied across the device, a much greater index difference is created and it is related to the external field E by:

$$N = N_1 - N_2 = N_{10} - N_{20} + 2AE + \ldots \quad (2)$$

The additional change in index is proportional to the external field. The linearity range is ultimately determined by the intrinsic properties of the electro-optic material. If a sufficient index difference is created between these two materials, according to the principle discussed above, the localization length becomes smaller than the size of the system and the protective device becomes highly reflective over a broad range of wavelengths.

On-State Performance

Figure 3A:
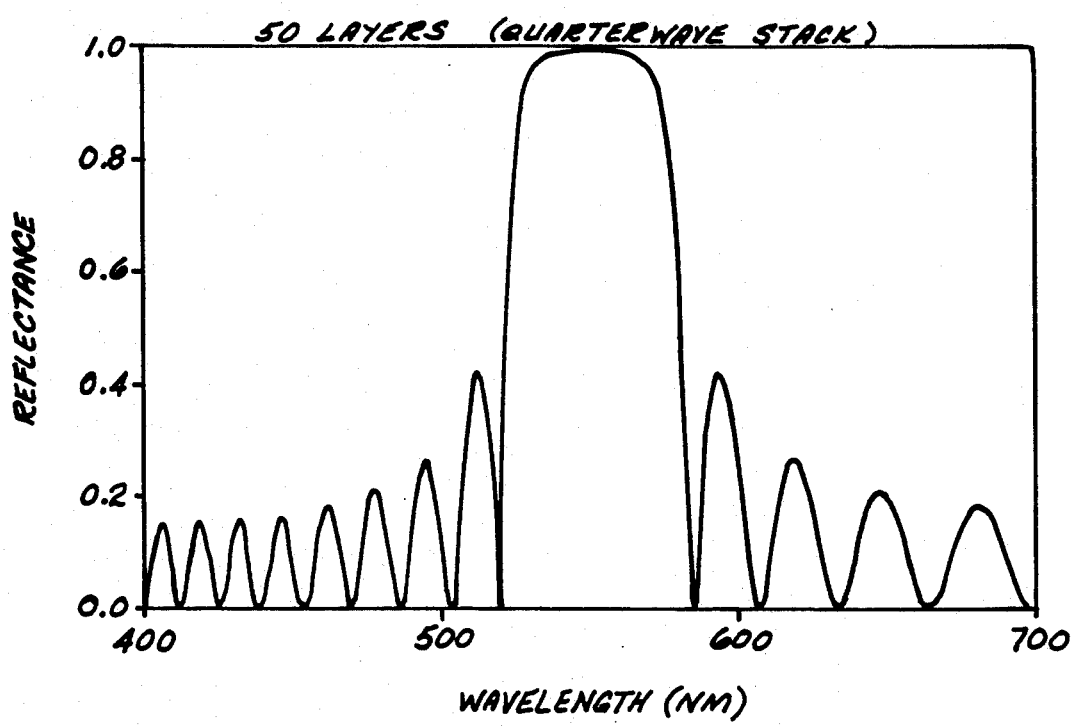
FIGS. 3A-B, 4A-D, and 5A-B are diagrams of reflectance vs. wavelength depicting spectral characteristics for several embodiments of the present invention.

As an example, the spectral characteristics of a quarterwave stack of 50 layers is computed. The high and low indices are assumed to be 1.6 and 1.4. The rejection wavelength is centered at 550 nm. The reflectance as a function of wavelength at normal incidence is shown in FIG. 3a.

Figure 3B:
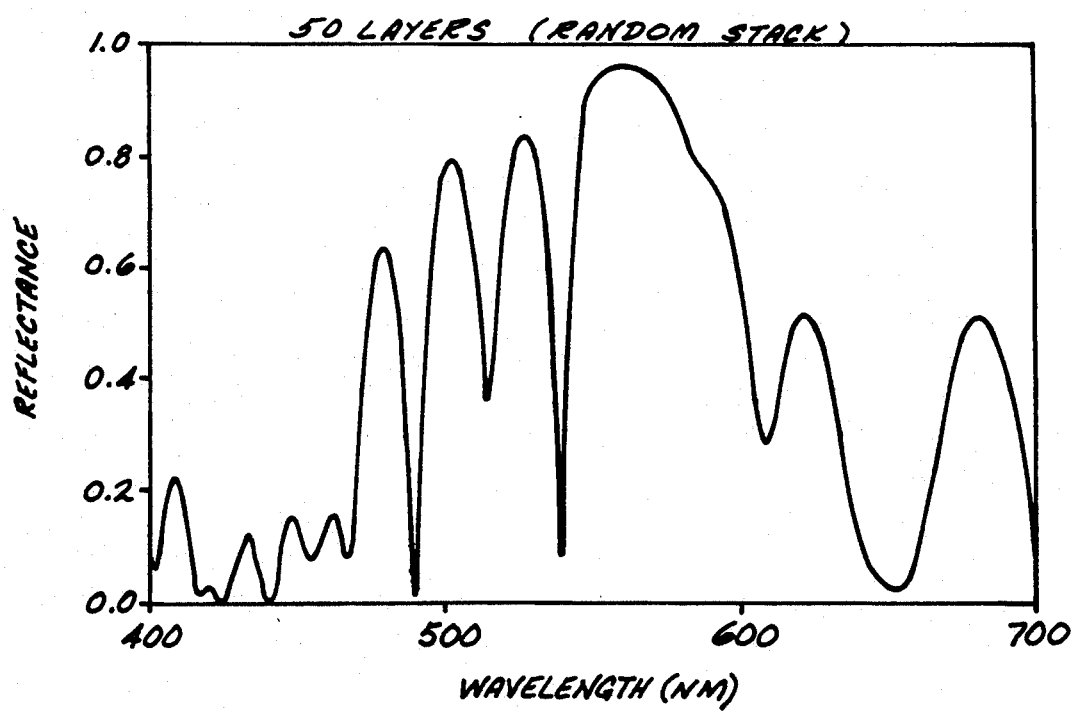
Figure 4A:
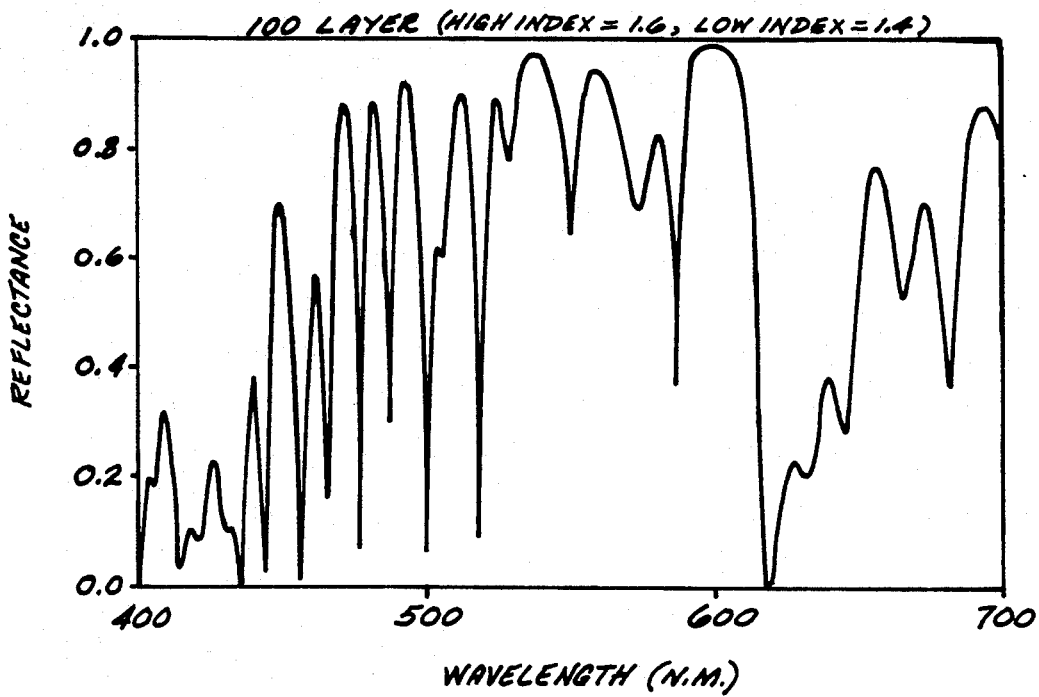
Figure 4B:
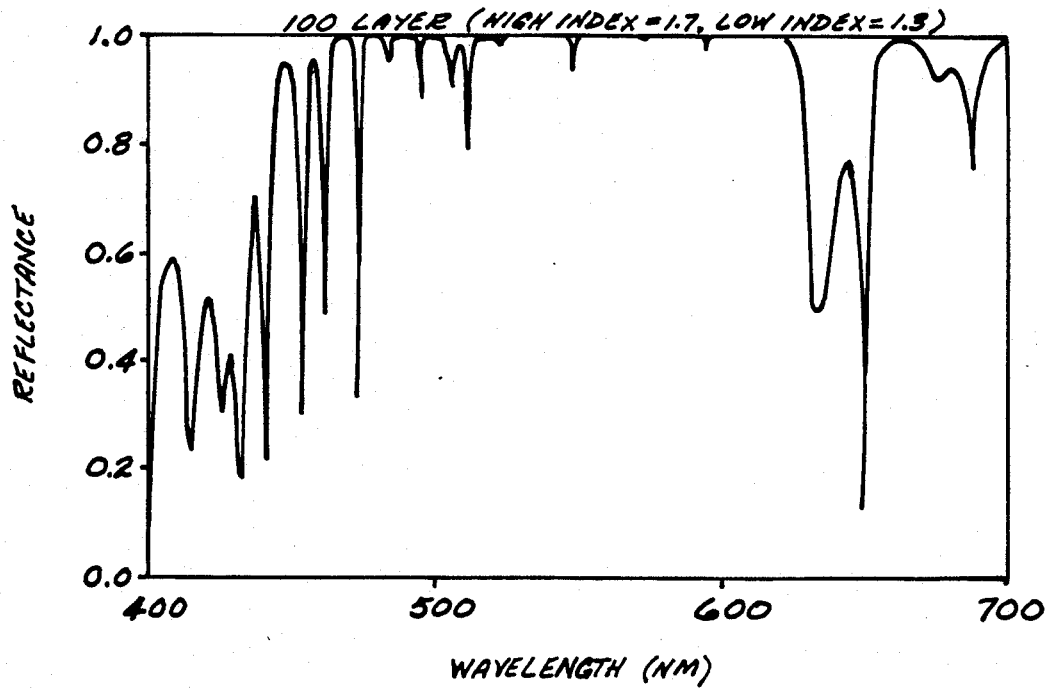
Figure 4C:
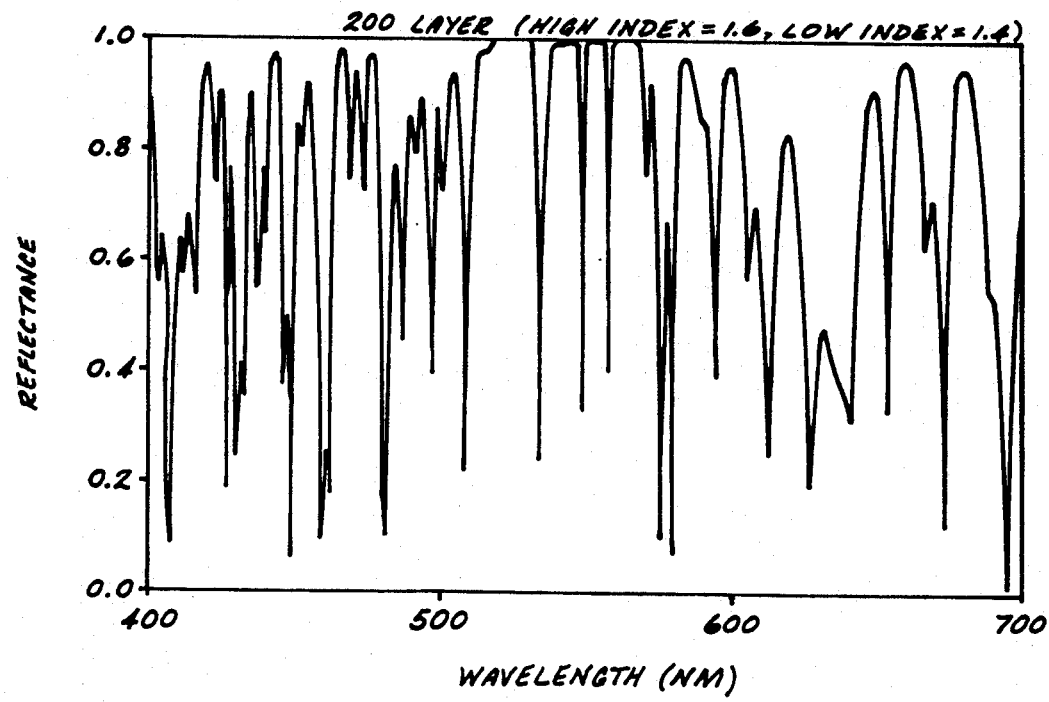
Figure 4D:
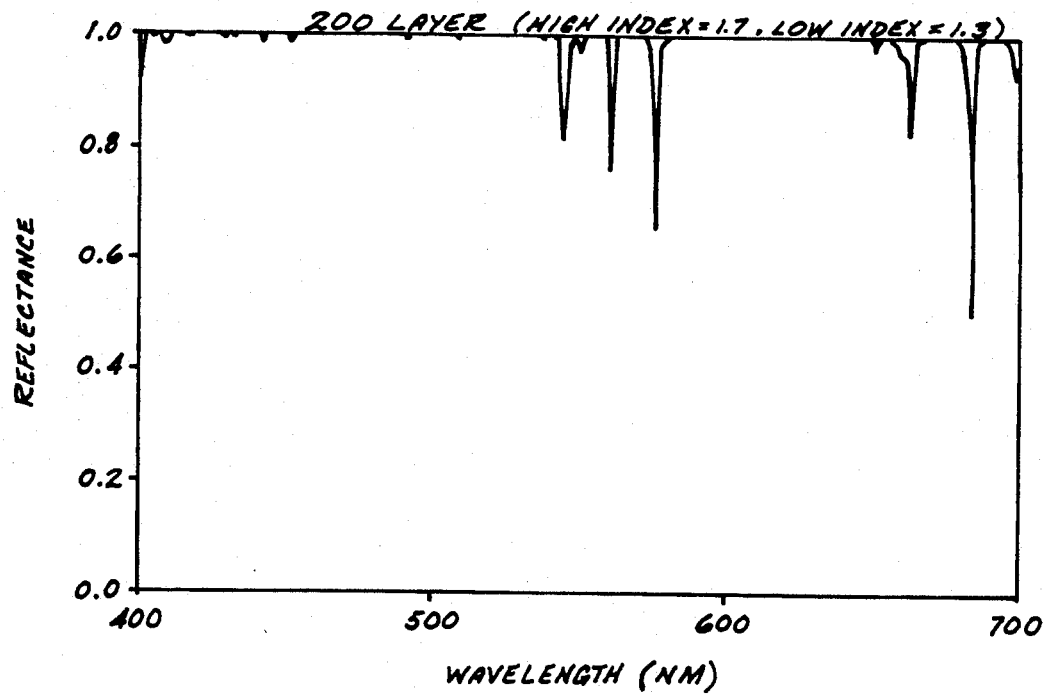

If the optical thickness distribution is changed to a uniform random distribution with the mid-point at D=137.5 nm (a quarter of 550 nm) and a fluctuation range from 0.75 D to 1.25 D, the resulting reflectance vs. wavelength plot is shown in FIG. 3b. By comparing FIG. 3b with FIG. 3a, it is clear that the rejection band has been broadened at the expense of a lower overall reflectance. The bandwidth can be furthered broadened by increasing the fluctuation range to from 0.5 D to 1.5 D. To cover the entire visible spectrum it is necessary to increase the index difference or the number of layers. The reflectance spectra of several additional embodiments and the results are shown in FIGS. 4a, b, c and d. FIGS. 4a and 4b are reflectance vs. wavelength curves for a 100 layer design with an index difference of 0.2 (high index=1.6, low index=1.4) and 0.4 (high index=1.7, low index=1.3) FIGS. 4c and 4d are the reflectance curves for a 200 layer design with an index difference of 0.2 and 0.4. From these results the following conclusions can be drawn:

(1) The overall reflectance can be increased by using more layers. However, this does not increase the bandwidth very dramatically, as can be seen by comparing FIG. 4a with 4c and FIG. 4b with 4d.

(2) An increased index difference can dramatically increase the overall reflectance and bandwidth, as can be seen by comparing FIG. 4a with 4b and 4c with FIG. 4d.

(3) The bandwidth also increases with an increasing range of thickness fluctuations. The wider the thickness fluctuation, the broader the reflection band. This can be seen by comparing FIG. 3a and FIG. 3b for the 50-layer design. This phenomenon has also been verified for the 100-layer and 200-layer designs.

Therefore, the on-state performance, i.e. bandwidth and overall reflectance is affected by the design and the dynamic range of the electro-optic materials. In principle, a rejection efficiency of 4 OD or more over the entire 400-140 nm band can be achieved. The performance of this invention is only limited by the index ranges of the materials. Because of the flat broad band response, the performance of the present invention is not only independent of the incident wavelength but also effectively independent of the angle of incidence.

Off-State Performance

Figure 5B:
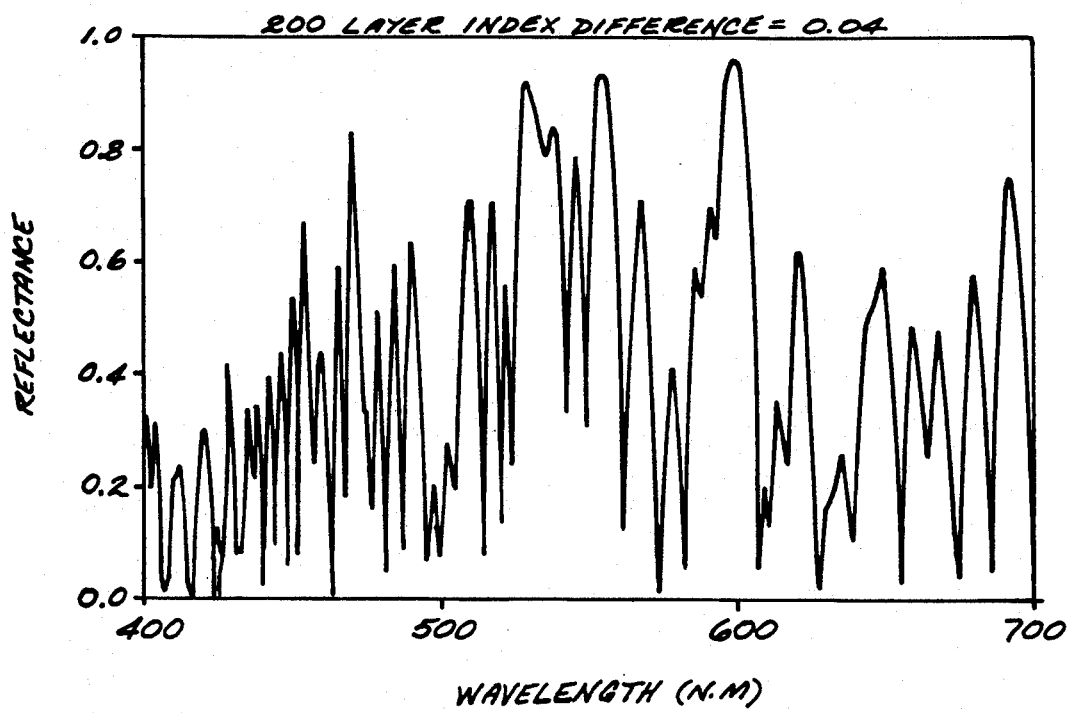
Figure 5A:
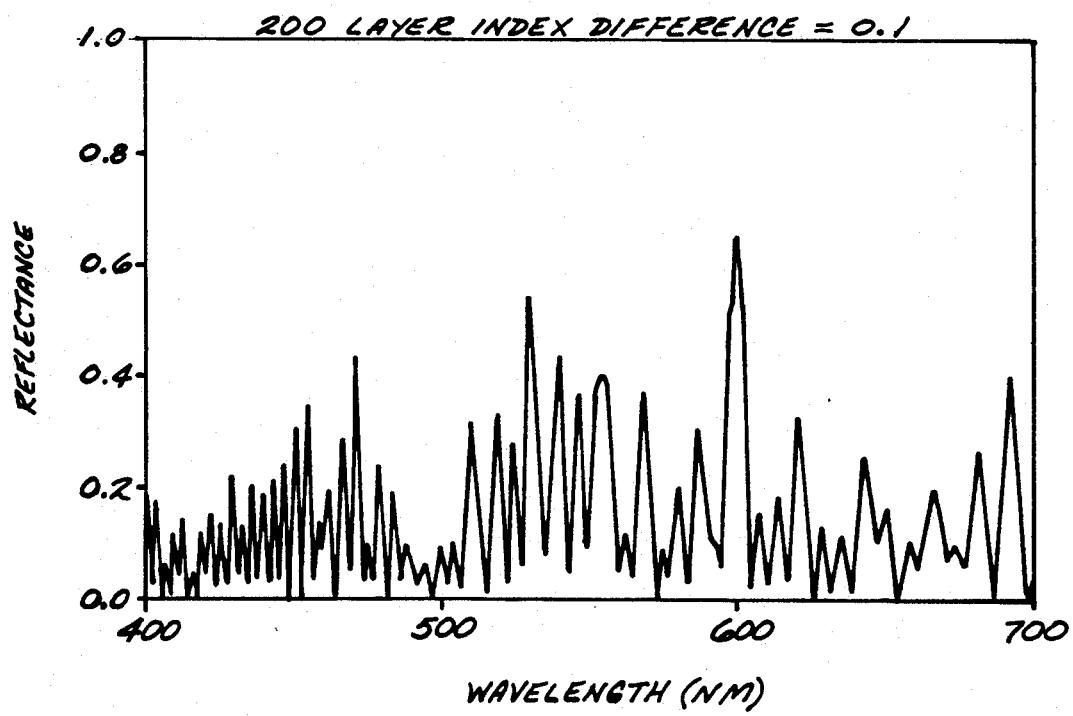

The off-state transmission is a very important issue for laser protection applications. In principle, if the two materials are perfectly index-matched in the absence of an external field, the off-state internal transmittance is 100%. However, as mentioned above, this may not be possible in practice. Therefore, it is important to calculate the transmission assuming that a finite index difference exists between the two materials. An additional embodiment of this invention is assumed to have 200 layers with a random thickness distribution centered at $D=137.5$ nm and having a fluctuation range of 0.5 D to 1.5 D. FIG. 5a shows the reflectance vs. wavelength curve assuming an index difference of 0.04 (high index=1.52 and low index=1.48). It can be seen from FIG. 5a that the off-state transmission is about 85%. If the index difference is increased to 0.1 (high index=1.55 and low index=1.45), the reflectance curve is shown in FIG. 5b. An overall transmission of about 50% is still obtained.

For laser eye protection a high scotopic and photopic transmittance is required. Since the eye is most sensitive to light at about 550 nm, a preferred embodiment of this invention should have the lowest reflectance at about 550 nm. On the other hand, it is desirable to have a uniform transmission over the 400-700 nm range so that no significant color distortion occurs in the off-state (in other words, the transmitted light shall have the same relative spectral distribution as the incident light throughout the visible spectrum).

Figure 6A:
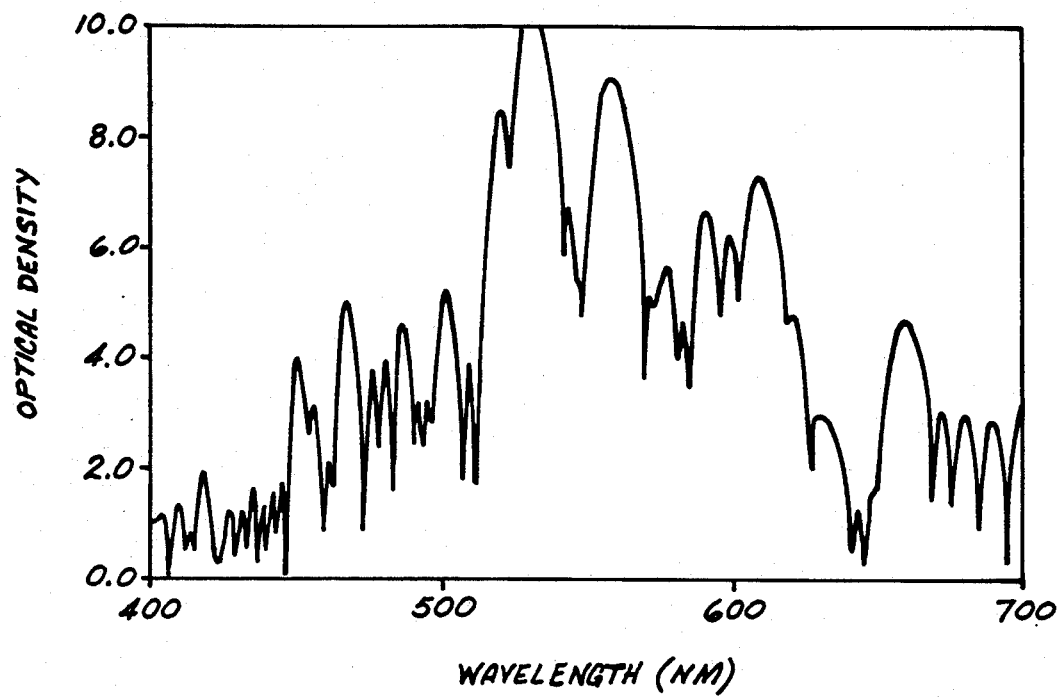
FIGS. 6A-B are diagrams of optical density vs. wavelength depicting spectral characteristics for additional embodiments of the present invention.
Figure 6B:
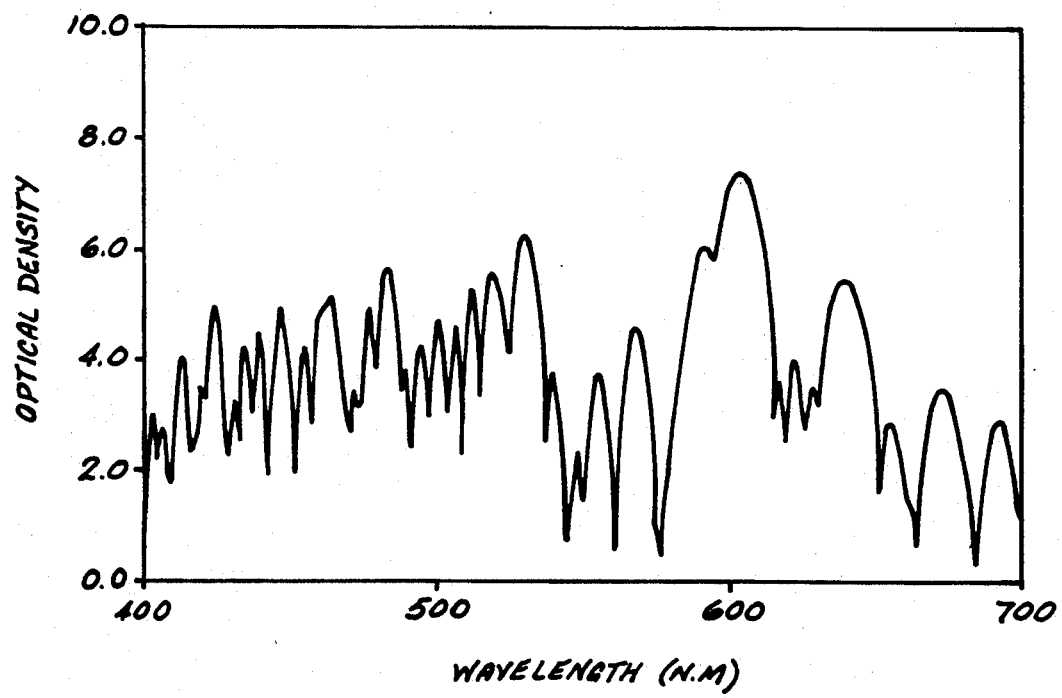
Figure 7:
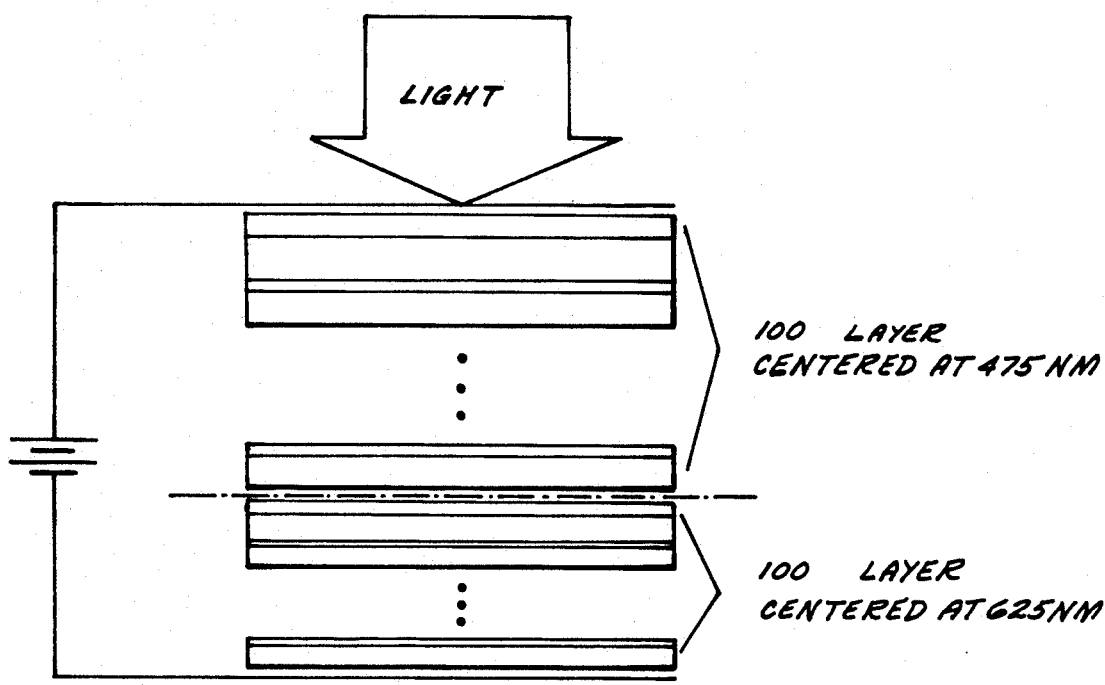
FIG. 7 is a diagrammatic cross-sectional elevation view, similar to FIG. 2, of still another embodiment of the present invention.

One of the advantages of the present invention is that the spectral Properties can be tailored to meet the specifications required by the application. For laser eye protection purposes, the several embodiments discussed above have several shortcomings such as a non-uniform reflectance and a large number of layers. The nonuniformity in the on-state reflectance can best be seen in the optical density (OD) vs. wavelength curve shown in FIG. 6a. The OD peaks at about 550 nm and falls off sharply on both sides. It is possible to alter this spectral response by optimizing the construction as shown in the preferred embodiment of FIG. 7. In FIG. 7, two 100-layer stacks are used to reflect light centered at 475 nm ((400+550)/2) and 625 nm ((550+700)/2) separately. Their combined OD curve is shown in FIG. 6b. By comparing FIG. 6b with FIG. 6a, it can be seen that a much more uniform response is achieved. The off-state reflectance is also more uniform. This implies a higher visual transmittance because the reflectance peaks are no longer centered at 550 nm. An added advantage is that during extended CW exposure, the device of FIG. 7 can still have about 50% transmission. This is accomplished by only activating the filter that covers the wavelength of the incident laser. Two sensors with two different sensitivity range, e.g., one covers 400-550 nm and the other covers 550-700 nm, may be required in order to determine the filter to be activated.

By using the construction of FIG. 7, the number of layers required for each filter is reduced to 100. This may have beneficial implications in terms of the fabrication yield because each filter can be fabricated separately. The number of layers of each filter can be further reduced by combining 3 or 4 individual stacks to cover the entire visible range. Beneficially, more uniform on-state and off-state reflectance are obtained. Since exact layer thickness control and uniformity control are not required in the fabrication process, it is feasible and economical to fabricate filters with a relatively large number of layers (100-200 layers). As discussed above, if electro-optic materials with greater dynamic ranges are used, the number of layers required can be reduced accordingly.

In the embodiments discussed above, only the thickness distribution was varied during the optimization process. It is known that a broad band reflector can also be achieved by having a random refractive index profile. The spectral performance of the present invention can thus be further enhanced by having both a random thickness distribution and a random index distribution. Furthermore, statistical distributions other than a uniform random distribution may also bring further enhancement to the spectral performance of this invention.

Electro-Optic Devices

As discussed above, the device of the present invention can be constructed using either electro-optic or nonlinear optical materials. Each approach has its advantages and disadvantages.

There are three primary advantages of using electro-optic materials to construct such a device. First, there are many well studied electro-optic (both inorganic and organic) materials available commercially with large electro-optic coefficients. Second, the processing techniques for these materials are partially established. And third, the excellent supporting electronics are widely available because similar electro-optic devices are commonly used in many optical systems such as Q-switches in laser systems and modulators in guided-wave devices.

Examples of suitable organic and inorganic electro-optic materials are set forth in TABLE I.

TABLE I.

Electro-Optic Properties of Some Commonly Used Materials

Inorganic $BaTiO_3$
$BiSi_{12}O_{20}$
$LiNbO_3$
$Sr_{0.75}Ba_{0.25}Nb_2O_6$

Organic 2-methyl r-nitroaniline
m-nitroaniline

Inorganic crystalline materials are preferred for use with the present invention because of their large electro-optic coefficients. The exact magnitude of the index modulation depends on the crystal orientation. A method which may be employed for depositing the electro-optic materials is magnetron sputtering. Since the material must be in the crystalline form, the thin film is deposited epitaxially to maintain its structure. Another approach is to convert the amorphous thin film into the crystalline form after the deposition process is completed. Transparent polycrystalline ceramics in the lanthanum-doped lead zirconate-titanate system (PLZT) have been grown and shown to have a large electro-optic coefficient. The substrates are normally quartz or sapphire plates.

Organic polymeric materials may also be preferred for constructing the electro-optic device of this invention. These materials are attractive in terms of their flexibility in forming various thin film structures. In principle, new molecules with large electro-optic coefficients can be engineered for optimal device performance. Furthermore, organic materials have smaller dielectric constants. This makes them better choices in terms of switching speed. Because of the flexibility in the control of molecular formation, several organic and polymeric materials are expected to have larger nonlinearities than their inorganic counterparts.

Noncentrosymmetry in the molecular structure is a prerequisite for obtaining second order non-linearity. Therefore, polymers containing, as part of their main or side chain, units with a large second order molecular hyperpolarizability are of the most use with this invention. Some of the most studied molecules are pNA (para-nitroaniline), MNA (2-methyl-4-nitraniline), DANS (4-dimethylamino-4'-nitrostilbene). In the microscopic level, these molecules must be aligned in order to preserve their molecular level nonlinearity.

Supporting Electronics and Speed

The overall speed of the laser protective device of this invention is limited only by the response of the driving electronics because the intrinsic speed of all materials is in the order of picoseconds or less. The speed of the electronics is essentially limited by the device capacitance. To reduce the capacitance, materials with smaller dielectric constants are required. From this perspective organic materials are preferred.

The configuration of the present invention may be very flexible because the basic principle only requires that the thickness or index distribution be random. The protective device may be construed in longitudinal and transverse configurations. The embodiments described above used a longitudinal configuration. The most flexible longitudinal configuration is a design having alternating layers of transparent electrodes and electro-optic/electro-mechanical materials. This construction allows the index or thickness or both of each layer to be controlled individually. Better device performance is expected to be obtained this way. The potential drawback is that a large number of transparent electrode layers is required, and the fabrication is more difficult.

Non-Linear Optical Materials

An important drawback of the electro-optic devices discussed above are the delay time in its electronic circuit and the requirement for an external power supply and sensors. These problems can be avoided by using nonlinear optical materials to construct the device. In this embodiment, the incident light itself creates the required index difference between the two layered materials and therefore self-activation can be achieved. The main benefit is the high speed (picosecond or less) that can be obtained by utilizing the nonlinear optical properties of the materials. The disadvantage is that its operation would require an optical concentrator.

The materials required for this application must possess a large third order nonlinear susceptibility $X^{(3)}$. Unlike $X^{(2)}$, which requires a noncentrosymmetric structure, the third order nonlinearity is present in all materials.

Materials exhibiting relatively large third order nonlinearities include:

TABLE II

| Symbol | Composition |
| --- | --- |
| pDA | polyacetylenes |
| pT | polythiophenes |
| pTT | polythienothiophene |
| pDTT | polydithienothiophene |

The response time of these materials is on the order of sub picoseconds.

FIG. 8 is a generallized schematic depicting a preferred embodiment of the present invention comprising a broad band mirror 12 comprised of electro-optic materials positioned in front of a sensor 14 (such as an eye). A circuit comprising a power supply 16 and switch 18 will dynamically switch mirror 12 between an on-state and an off-state in response to a detector 20. Preferably, detector 20 is a laser detector such as the laser detectors described in U.S. Pat. Nos. 3;824,018, 4,536,089 or 4,600,307. During use, broad band mirror 12 will normally be in the off-state and exhibit a high degree of transmittance to sensor 14. However, in the event that laser detector 20 detects laser light, then switch 18 will be actuated thereby placing mirror 12 in an on-state and thus preventing the laser from impinging upon sensor 14.

FIG. 9 is a generallized schematic depicting a preferred embodiment of the present invention comprising a broadband mirror 12' comprised of nonlinear optical materials. In this embodiment, mirror 12' is sandwiched between a pair of lens 22 and 24, all of which is positioned in front of sensor 14'. As described above with regard to the nonlinear optical materials, mirror 12' will dynamically and self-actively switch between an on-state and an off-state in response to changes in the oncoming incident light.

Even though the protective device of the present invention has been described in terms of a sensor (eye) protection, there are potential applications in other areas of optics. These include: windows, shutters, beam splitters, modulators and spatial light modulators. For example, in optical communications, this device can be used a broad band modulator or shutter. In laser technologies, this device can be used as a broad band Q-switch in a tunable laser system or as a variable end reflector, etc. Because of its broad band nature and its high transmission in the off-state (contrary to polarizer-/analyzer where the maximum off-state transmission is 50% for unpolarized incoming light), this device is uniquely suited for numerous applications in modern optics, While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. Laser protective filter comprising:
   a plurality of layers in a stack defining a multilayer stack;
   switch means for dynamically switching between a transparent state wherein said stack is substantially transparent and a reflective state wherein said stack is substantially reflective over a broadband;
   the refractive index of said layers being substantially the same in said transparent state and the refractive index between adjacent layers being different in said reflective sate; and
   said layers each being of different optical thickness and said layers of different thickness being randomly arranged with the number of said layers being selected so as to make said multilayer stack function as a broadband reflector in said reflective state.

2. The filter of claim 1 wherein:
   said layer include a combination of layers having a fixed refractive index and layers comprising electro-optic materials.

3. The filter of claim 1 wherein:
   said layers include a combination of layers comprising a first electro-optic material and at least one second electro-optic material.

4. The filter of claim 1 wherein:
   at least a portion of said layers comprise electro-optic materials.

5. The filter of claim 4 wherein:
   said electro-optical materials are selected from the group consisting of $BaTiO_3$, $BiSi_{12}O_{20}$, $LiNbO_3$, $Sr_{0.75}Ba_{0.25}Nb_2O_6$-methyl r-nitroaniline and m-nitroaniline.

6. The filter of claim 1 wherein:
   said layers include a combination of layers having a fixed refractive index and layers comprising nonlinear optical materials.

7. The filter of claim 1 wherein:
   said layers include a combination of layers comprising a first nonlinear optical material and at least one second nonlinear optical material.

8. The filter of claim 1 wherein:
   at least a portion of said layers comprise nonlinear optical materials.

9. The filter of claim 8 wherein:
   said non-linear optical materials are selected from the group consisting of polyacetylenes, polythiophenes, polythienothiophene and polydithienothiophene.

10. The filter of claim 1 wherein:
    said dynamic switching is actuated by an external electric field.

11. The filter of claim 10 wherein:
    said stack has surfaces and including transparent electrodes on said surfaces for applying said electric field.

12. The filter of claim 10 including:
    a plurality of transparent electrode layers embedded in said device for applying said electric field.

13. The device of claim 1 wherein:
    said dynamic switch is actuated by light intensity.

14. The filter of claim 1 including:
    laser detector means communicating with said switch means wherein said laser detector means actuates said switch means upon the detector of laser light.

15. The filter of claim 1 including:
    first and second spaced lens, said multilayer stack being sandwiched between said first and second lens.

16. The filter of claim 15 wherein:
    at least a portion of said layers comprise nonlinear optical materials.

* * * * *

UNITED STATES PATENT AND TRADEMARK OFFICE
CERTIFICATE OF CORRECTION

PATENT NO. : 5,212,585
DATED : May 18, 1993
INVENTOR(S) : Ning Xiaohui

It is certified that error appears in the above-identified patent and that said Letters Patent are hereby corrected as shown below:

On the Title Page
In the Abstract, line 5, after "90" insert %.
Column 1, line 23, delete "Plastics" and insert therefor --plastics--
Column 3, line 53, after "well.", insert a new paragraph
Column 3, Equation (1b), delete "N(E)", and insert therefor --$N_2(E)$--
Column 4, line 55, insert a period --.-- after "=1.3)"
Column 5, line 48, delete "Properties" and insert therefor --properties--
Column 9, line 15, delete "sate" and insert therefor --state--
Column 9, line 23, delete "layer" and insert therefor --layers--
Column 9, line 36, delete "$Sr_{0.75}Ba_{0.25}Nb_2O_6$-methyl" and insert therefor --$Sr_{0.75}Ba_{0.25}Nb_2O_6$, 2-methyl--

Signed and Sealed this

Tenth Day of April, 2001

Attest:

NICHOLAS P. GODICI

*Attesting Officer*    Acting Director of the United States Patent and Trademark Office